(12) United States Patent
Davis et al.

(10) Patent No.: US 7,487,059 B2
(45) Date of Patent: Feb. 3, 2009

(54) TRANSDUCER HEALTH DIAGNOSTICS FOR STRUCTURAL HEALTH MONITORING (SHM) SYSTEMS

(75) Inventors: Christopher L. Davis, Maple Valley, WA (US); Justin D. Kearns, Seattle, WA (US); V. John Mathews, Mercer Island, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 11/766,445

(22) Filed: Jun. 21, 2007

(65) Prior Publication Data

US 2008/0319692 A1 Dec. 25, 2008

(51) Int. Cl.
 *G06F 19/00* (2006.01)
(52) U.S. Cl. .................................. 702/116; 702/85
(58) Field of Classification Search .................. 702/116
 See application file for complete search history.

(56) References Cited

U.S. PATENT DOCUMENTS 5,446,682 A * 8/1995 Janke et al. ................... 702/85

OTHER PUBLICATIONS

Adrian Cuc et al.; Disbond detection in adhesively-bonded structures using piezoelectric wafer active sensors; 2004, pp. 66-77, vol. 5394; Proc. of SPIE.

James K. Blackshire et al.; Characterization of Sensor Performance and Durability for Structural Health Monitoring Systems; 2005; pp. 66-75, vol. 5770, Proc. of SPIE.
James K. Blackshire et al.; Characterization and Modeling of Bonded Piezoelectric Sensor Performance and Durability in Simulated Aircraft Environments; 2006.
P.M. Flanagan et al.; Developing a Self-Diagnostic System for Piezoelectric Sensors; 1990; pp. 1-5, AIAA/SAE/ASME/ASEE 26th Joint Propulsion Conference, Orlando, FL.
Victor Giurgiutiu et al.; Damage Detection in Thin Plates and Aerospace Structures with the Electro-Mechanical Impedance Method; 2005; pp. 99-117, vol. 4(2), SHM, Sage Publications.
Victor Giurgiutiu et al.; Embedded Self-Sensing Piezoelectric Active Sensors for On-Line Structural Identification; 2002; pp. 116-125, vol. 124, ASME.
Timothy G.S. Overly et al.; Development of Signal Processing Tools and Hardware for Piezoelectric Sensor Diagnostic Processes.
Gyuhae Park et al.; Performance assessment and validation of piezoelectric active-sensors in structural health monitoring, 2006; pp. 1673-1683, vol. 15, Smart. Mater Struct., IOP Publishing LTd.

* cited by examiner

*Primary Examiner*—Bryan Bui
*Assistant Examiner*—Jonathan Teixeira Moffat
(74) *Attorney, Agent, or Firm*—Charles L. Moore; Moore & Van Allen, PLLC

(57) ABSTRACT

A method for diagnosing the health of a transducer may include transmitting a signal to a transducer to cause the transducer to transmit a stress wave into an object being monitored, wherein the signal has a predetermined frequency range or bandwidth. The method may also include receiving response data for the transducer and transforming the response data to data representative of an impedance curve of impedance versus frequency for the predetermined frequency range. The method may further include extracting selected parameters from the impedance curve to diagnose the health of the transducer.

37 Claims, 4 Drawing Sheets

TRANSDUCER HEALTH DIAGNOSTICS FOR STRUCTURAL HEALTH MONITORING (SHM) SYSTEMS

BACKGROUND OF THE INVENTION

The present invention relates to monitoring or investigating the structural health of a structure or object, and more particularly to transducer health diagnostics for piezoelectric based structural health monitoring or management (SHM) systems.

New, lightweight composite materials, traditional metallic materials, and other materials are being used and optimized in designs more extensively in the aerospace industry for commercial aircraft and other aerospace vehicles, as well as in civil infrastructure, ground transportation, and other industries. The new materials and new designs may be subject to extreme stresses or potential damage from an impact or other cause. For example near a fuselage cargo door surround of a commercial aircraft, baggage handlers often inadvertently collide with and cause impact damage to the airplane fuselage. Any such damage needs to be quickly and efficiently identified, located, and the size and extend determined so that any needed repairs can be performed and to reduce airplane maintenance costs and eliminate airplane cancellation and delays. To implement quick non-destructive evaluations that may be performed quickly to ensure minimal maintenance times, numerous transducers or sensors are required to transmit and receive signals to detect any anomalies or damage. Transmitted and received signal quality can directly affect overall damage or anomaly detection and mapping performance. Accordingly, being able to differentiate between "good" transducers and "bad" transducers can significantly improve the fidelity and reliability of SHM systems since the transducers themselves and the bond of the transducers to the structure are also susceptible to damage.

BRIEF SUMMARY OF THE INVENTION

In accordance with an embodiment of the present invention, a method for diagnosing the health of a transducer may include electrically exciting a transducer to cause the transducer to transmit a stress wave into a structure being monitored, wherein the signal has a predetermined frequency range or bandwidth. The method may also include electrically exciting a transducer and receiving response data for the transducer and transforming the response data to obtain impedance versus frequency curve for the predetermined frequency range. The method may further include extracting selected parameters from the impedance versus frequency curve to diagnose the health of the transducer.

In accordance with another embodiment of the present invention, a method for monitoring the structural health of an object or structure may include transmitting a signal to each of a plurality of transducers to cause each transducer to transmit a stress wave into the object or structure being monitored, wherein the signal has a predetermined frequency range or bandwidth. The method may also include measuring a time domain voltage across each transducer and a time domain current. The method may additionally include transforming these measurements into the frequency domain over the predetermined frequency range for each transducer to generate data representative of an impedance curve. The method may further include extracting selected parameters from the impedance curve of each transducer to diagnose the health of each transducer.

In accordance with another embodiment of the present invention, a system for monitoring the structural health of an object or structure may include a plurality of transducers mounted to the object or structure at chosen locations. The system may also include a data acquisition unit electrically connected to each of the transducers. The system may further include a module to diagnose a health of each transducer.

In accordance with another embodiment of the present invention, a computer program product for diagnosing the health of a transducer may include a computer usable medium having computer usable program code embodied therewith. The computer usable medium may include computer usable program code configured to transmit a signal to each of a plurality of transducers to cause each transducer to transmit a stress wave into the object or structure being monitored, wherein the signal has a predetermined frequency range or bandwidth. The computer usable medium may also include computer usable program code configured to measure a time domain voltage across each transducer and a time domain current. The computer usable medium may further include computer usable program code configured to transform the time domain voltage and current into frequency domain impedance over the predetermined frequency range for each transducer to generate data representative of an impedance curve of impedance versus frequency over the predetermined frequency range for each transducer. The computer usable medium may yet further include computer usable program code configured to extract selected parameters from the impedance curve of each transducer to diagnose a health of each transducer.

Other aspects and features of the present invention, as defined solely by the claims, will become apparent to those ordinarily skilled in the art upon review of the following non-limited detailed description of the invention in conjunction with the accompanying figures.

DETAILED DESCRIPTION OF THE INVENTION

Figure 1:
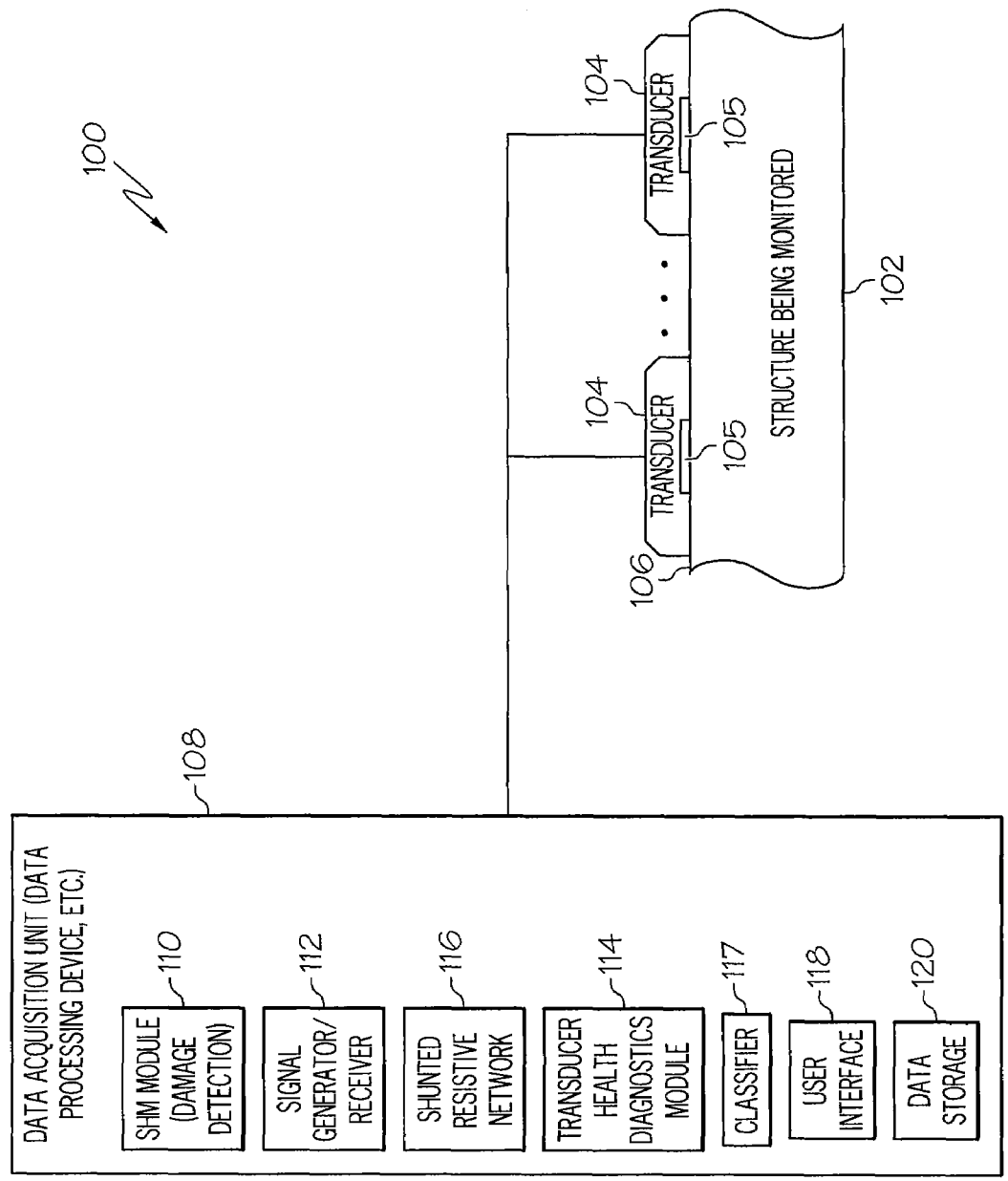
FIG. 1 is a block schematic diagram of an example of a system for structural health monitoring (SHM) of a structure in accordance with an embodiment of the present invention FIGS. 2A-2B (collectively FIG. 2) are a flow chart of an exemplary method for determining or diagnosing the health of transducers in a SHM system in accordance with an embodiment of the present invention.

The following detailed description of embodiments refers to the accompanying drawings, which illustrate specific embodiments of the invention. Other embodiments having different structures and operations do not depart from the scope of the present invention.

As will be appreciated by one of skill in the art, the present invention may be embodied as a method, system, or computer program product. Accordingly, portions of the present invention may take the form of an entirely hardware embodiment, an entirely software embodiment (including firmware, resident software, micro-code, etc.) or an embodiment combining software and hardware aspects that may all generally be referred to herein as a "circuit," "module," "unit," or "system." Furthermore, the present invention may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a tangible medium such as a portable computer diskette, a hard disk, a random access memory (RAM), a read-only memory (ROM), an erasable programmable read-only memory (EPROM or Flash memory), an optical fiber, a portable compact disc read-only memory (CD-ROM), or other tangible optical or magnetic storage devices; or transmission media such as those supporting the Internet or an intranet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Computer program code for carrying out operations of the present invention may be written in an object oriented programming language such as Java, Smalltalk, C++ or the like. However, the computer program code for carrying out operations of the present invention may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

FIG. 1 is a block schematic diagram of an example of a system 100 for structural health monitoring (SHM) of a structure 102 or object in accordance with an embodiment of the present invention. The structure 102 or object may be an aircraft, ground transportation, watercraft, civil structure or other vehicle or structure. A plurality of transducers 104 may be mounted or attached by bonding or other means to a surface 106 of the structure 102 being monitored or tested. One practical implementation of such a SHM system as the exemplary system 100 requires that the transducers 104 are attached or bonded to a structure and are used for inspecting damage in the structure for maintenance reasons or quick detection and assessment of damage. Since the transducers 104 also experience the same environment as the host structure and thus are susceptible to damage.

The transducers 104 may be attached at predetermined strategic locations on the surface 106, such as around or relative to critical structural elements, such as cargo doors or other access points on an aircraft that may be susceptible to impacts and possible damage. An example of a transducer that may be used for transducers 104 is described and claimed in U.S. patent application Ser. No. 11/754,167, entitled "Structural Health Monitoring (SHM) Transducer Assembly and System", filed May 25, 2007, which is assigned to the assignee as the present application and incorporated herein in its entirety by reference. Each transducer 104 or sensor includes a piezoelectric disk 105 capable to transmitting stress waves into the structure 102 and receiving responsive signals and/or any back scatter from any anomalies or damage in the structure 102. The transducers 104 may be attached to the structure 102 by a conductive or a non-conductive adhesive (not shown in the drawings) similar to that described in U.S. patent application Ser. No. 11/754,167.

The transducers 104 may require replacement during the life of the system 100, depending upon the extent of any damage to the transducers 104. It is not ideal, nor cost beneficial, if the SHM system 100 requires maintenance (i.e. transducer replacement) every time a SHM measurement indicates some sign of degradation. Accordingly, the transducer diagnostics method should be capable of determining whether or not a transducer shall be used in the SHM damage assessment. A full characterization of the extent that a transducer defect or damage has on the SHM system performance is desirable. SHM system performance may be defined as the accuracy of predicting or determining a location and size of any anomalies or damage. If damaged sensors are detected, the sensors will not be used in the damage assessment, and when the timing is appropriate, the damaged sensors or sensor installations will be replaced.

The transducers 104 may be electrically connected to a data acquisition unit 108. As described herein, the data acquisition unit 108 may send voltage signals to the transducers 104 to cause the transducers to transmit a structural stress wave or waves into the structure 102 and to receive a voltage response to the stress waves to detect any damage or anomalies in the structure 102. The data acquisition unit 108 may be a data processing device, computing device or similar hardware device programmed to perform the functions described herein.

The data acquisition unit 108 may include a structural health monitoring (SHM) or damage detection module 110 to analyze the data received from the transducers 104 to detect and map any anomalies or damage in the structure 102. A signal generator or transmitter and receiver 112 may be associated with the SHM module 110 to generate particular types of signals to the transducers 104 to cause the transducers to transmit the stress waves into the structure 102 and to receive the responsive signals or data from the transducers 104. The signal generator/transmitter and receiver 112 may also be integrated into the SHM module 110.

The data acquisition unit 108 may also include a transducer health diagnostic module 114 to diagnose the health of each transducer 104 which may include determining a state of being or condition of each transducer. Diagnosing the health of each transducer 104 may also include determining if the transducer is functioning properly; that the electrical connection to the transducer is not faulty; the piezoelectric disk 105 is not cracked; the transducer assembly 104 is properly electromechanically attached or coupled to the surface 106 of the structure 102; or whether some other condition exists that may affect any transducers ability to accurately and reliably predict damage in the structure 102.

Results from the transducer diagnostics module 114 may feed into and directly affect the overall flow of the SHM system protocol since a faulty transducer included in a damage identification and mapping process (block 110) may produce a false positive/negative indication or result in the reduction of the accuracy of the damage detection output. The transducer diagnostic module 112 may qualify each transducer 104 as functioning or non-functioning. If any transducer 104 has completely failed, the transducer is preferably replaced at the next scheduled maintenance check for the structure 102, aircraft or other object. If the transducer 104 is functioning, the transducer health diagnostics module 114 may output the raw parameters as measured by the diagnostic system 100 or a percent change in the measured parameters of the diagnostic system 100 as compared to previous transducer diagnostics check. If one or a combination of measured parameters is classified as unhealthy, then that transducer shall be disregarded in the current particular damage assessment of the structure 102. A classifier or classification module 117 may be provided to perform the classification. Classification could occur by one or more of the following methods: setting predetermined limits, a Bayesian neural network, any rule-based algorithm or other classification method. Transducer health may be defined as overall transducer efficiency of the conversion of electrical energy into mechanical energy and vice versa. This efficiency is most commonly observed to degrade appreciably when either of two failure modes occurs: transducer disbanding and transducer or piezo cracking.

The transducer health diagnostics module 114 may utilize a shunted resistive network 116 to measure a time domain voltage across each transducer 104 and a time domain current through each transducer 104. As described in more detail herein, the time-varying voltage and the time-varying current are then transformed into the frequency domain and used to obtain the impedance curve for each transducer 104 over a predetermined frequency range or bandwidth for diagnosing transducer health.

The data acquisition unit 108 may further include a user interface 118 to permit a user to control operation of the system 100. The user interface 118 may also provide information relative to the health of each transducer 104 in addition to information relative to the structural health of the structure 102 or object being monitored, as well as other information useful for structural health monitoring. The user interface may include input and output devices, such as a keyboard, monitor, printing device, computer media drive devices and the like.

The data acquisition unit 108 may also include a data storage device 120. The data storage device 120 may store information or data related to transducer health for statistical analysis; information or data related to monitoring the structural health of the structure 102 as described herein; or other data. The data storage device 120 may also be a remote storage device or a separate storage device and not a element of the data acquisition unit 108.

Figure 2A:
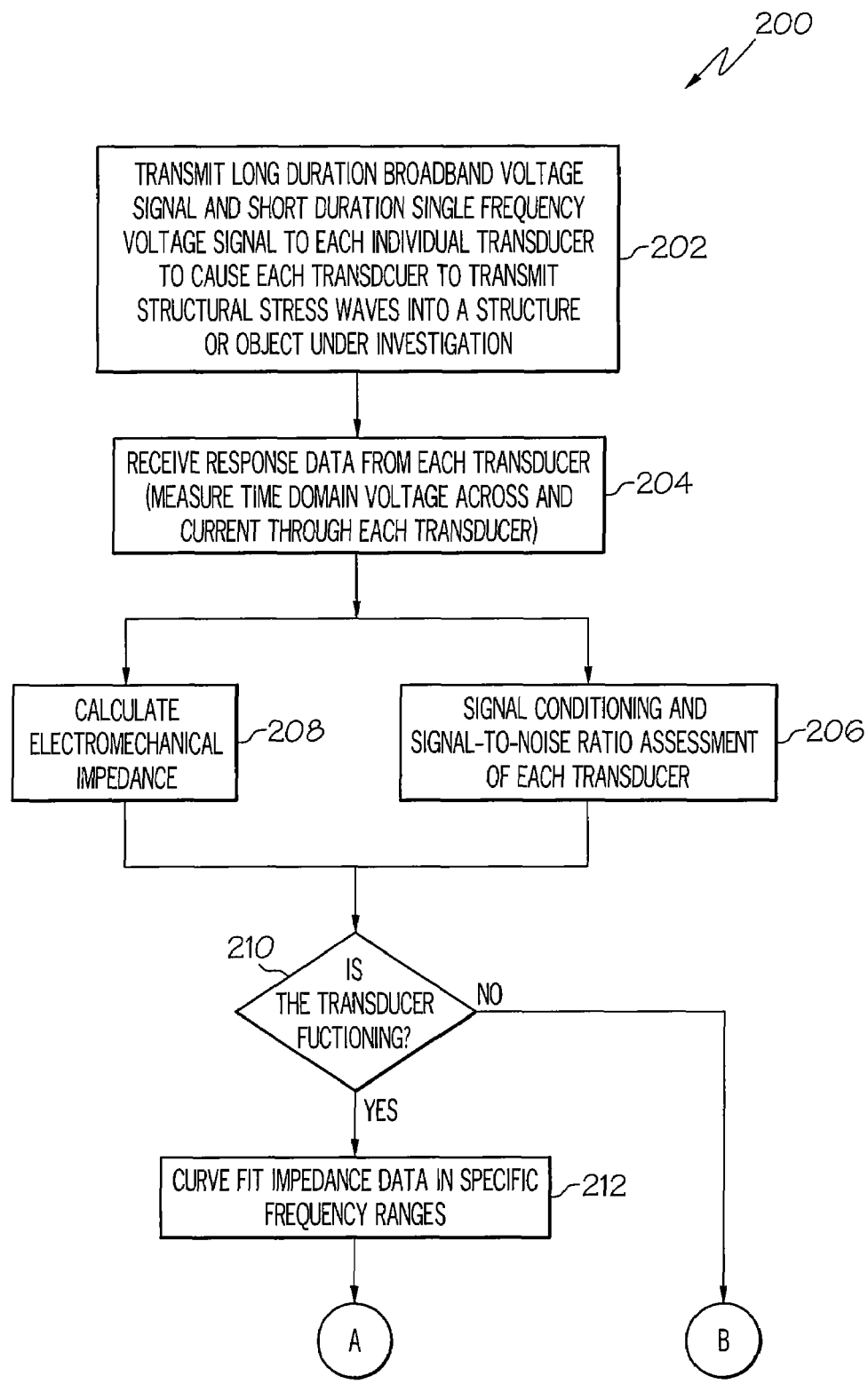
Figure 2B:
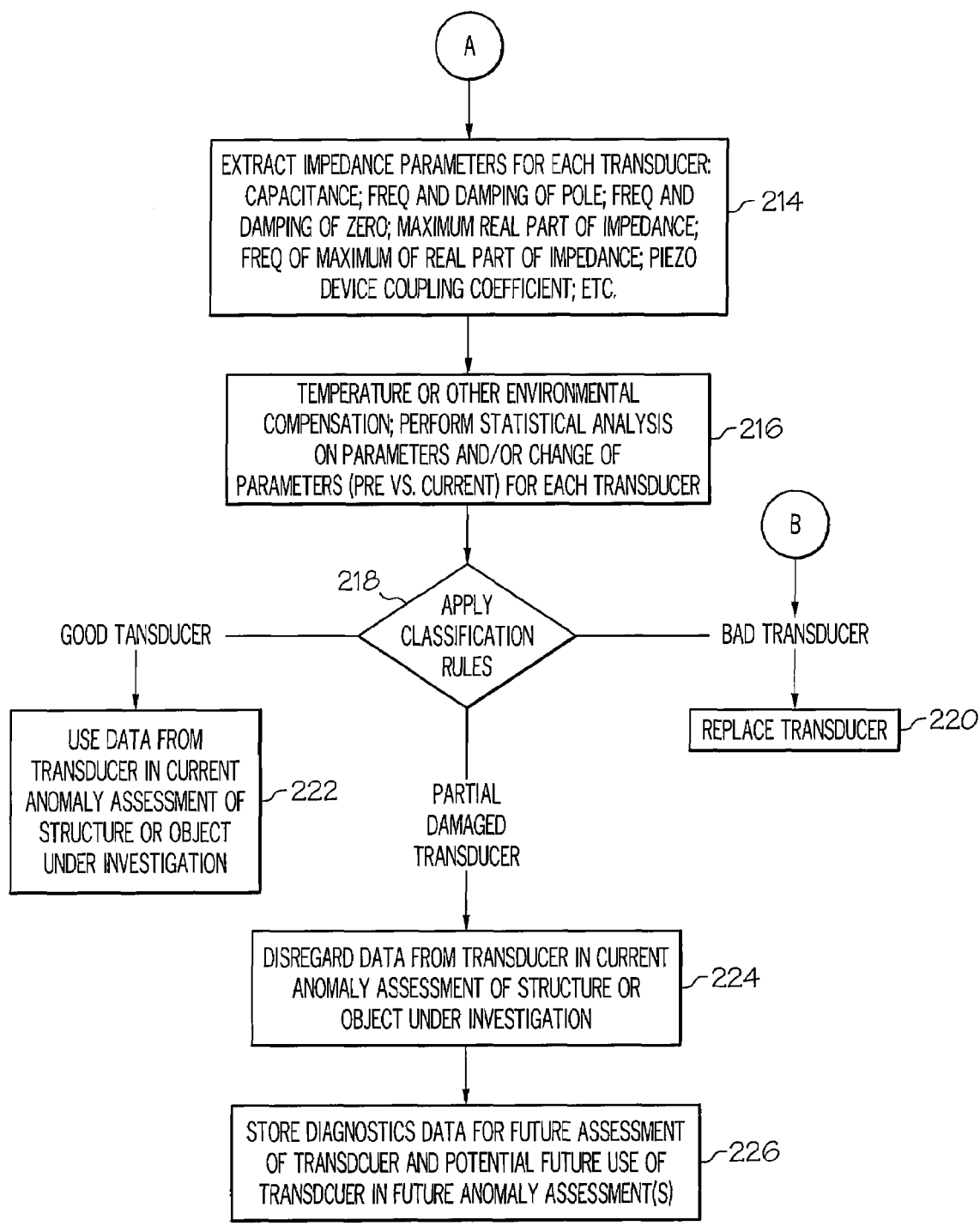

FIG. 2A-2B (collectively FIG. 2) are a flow chart of an exemplary method 200 for determining or diagnosing the health of transducers in a SHM system in accordance with an embodiment of the present invention. The method 200 may be embodied in the transducer health diagnostic module 114 of FIG. 1. In block 202, a signal having a predetermined frequency range or bandwidth may be sent to each transducer to cause the respective transducers to transmit a stress wave into an object or structure, such as structure 102 in FIG. 1, under investigation or being monitored. The signal may be a long duration broadband electrical voltage signal. The signal may have a bandwidth of about 100 Hertz to about 1.5 Mega Hertz. The voltage signal is sent through wiring to the piezoelectric component (for example piezoelectric disk 105 in FIG. 1) of the transducer thus exciting several electromechanically coupled response modes.

In block 204, response data or signals may be received from each transducer. Time domain voltage across and current through each transducer may be measured. As previously described, a data acquisition unit, such as unit 108 of FIG. 1, may utilize a shunted resistive network to measure the current through as well as voltage across each transducer.

In block 206, a conditioning and signal-to-noise assessment of each transducer may be performed. A signal processing approach may be utilized to potentially detect any transducers which may be either non-functioning or damaged. The approach considers two different types or classes of damaged sensors or transducers. In the first class, an assumption is made that the transducer was good when any baseline data was acquired, but the transducer was damaged during a time between the acquisition of the baseline data and acquisition of the test data. If there is a difference larger than a predefined threshold in the signal-to-noise ratio (SNR) of the test signals when compared with the SNR of the baseline signal, the transducer, wiring, or other failure has occurred or there exists a potentially defective or damaged part of the system. Accordingly, transducers which exhibit a large differential (larger than the predefined threshold) in SNR between baseline data and test data may be flagged as non-functioning. The predefined threshold may be about 5 decibels (dB); although, the threshold may change with the structure and signal properties.

In the second class of damages, an assumption is made that the transducer was damaged for both the baseline and test measurements. In such cases, transducers that exhibit low signal-to-noise ratios may be flagged as non-functioning.

In block 208, the time-domain voltage across the transducer and time-domain current through each transducer are transformed into the frequency domain to obtain electrical impedance for each transducer. Accordingly, the current and voltage response data received from each transducer may be transformed into data representative of an impedance curve of impedance versus frequency for the predetermined frequency range or bandwidth.

In block 210, a determination may be made whether the transducer is functioning based on the SNR assessment in block 206 and an initial investigation of the impedance data from block 208. If the determination is made in block 210 that the transducer is not functioning, i.e. the transducer has no response to the electrical inputs as judged by block 210, the method 200 may advance to block 220 and the non-functioning transducer may be replaced or the particular wiring failure or other failure for that channel may be repaired. If the transducer is functioning in block 210, the method 200 may advance to block 212.

In block 212, data may be generated representative of a curve or plot of impedance versus frequency over the predetermined frequency range or bandwidth for each transducer. The steady-state forced vibration solution of the governing equation of motion of a radial piezo disk as described in Giurgiuitiu, V. and A. Zagrai, "Damage Detection in Thin Plates and Aerospace Structures with the Electro-Mechanical Impedance Method", 2005, Structural Health Monitoring, Vol. 4 (2) gives a measure of electrical impedance as a function of driving frequency as:

$$Z(s) = \frac{1}{i\omega C}\left[\frac{\phi\frac{J_0}{J_1} - (1-v) - \psi(1+v)}{(1-k_p^2)\left(\phi\frac{J_0}{J_1} - (1-v) - \psi(1+v) + k_p^2(1+v)\right)}\right] \quad \text{Eq. 1}$$

In Equation 1, Z(s) is impedance and ω is radian frequency. C is capacitance and a function of piezo permittivity, disk radius, and disk thickness. $k_p$ is the device coupling coefficient, $J_0$ and $J_1$ are first and second order Bessel functions, v is the piezo Poisson's ratio, $\phi$ is a function of frequency, disk radius, planar modulus, and density, $\psi$ is the complex stiffness ratio of the structure to the piezo. These features or elements of Equation 1 contain information specific to the mechanical properties of the piezoelectric disk, adhesive used to surface-bond the disk, and the electrical connection to the transducer. Fitting the impedance data to assume the analytical form above over a broadband spectrum is difficult due to the nature of the Bessel functions and complex numbers. An alternative method to extract physical piezo properties is to curve fit in narrow-band frequency regimes, as will be described with reference to FIG. 3.

Figure 3:
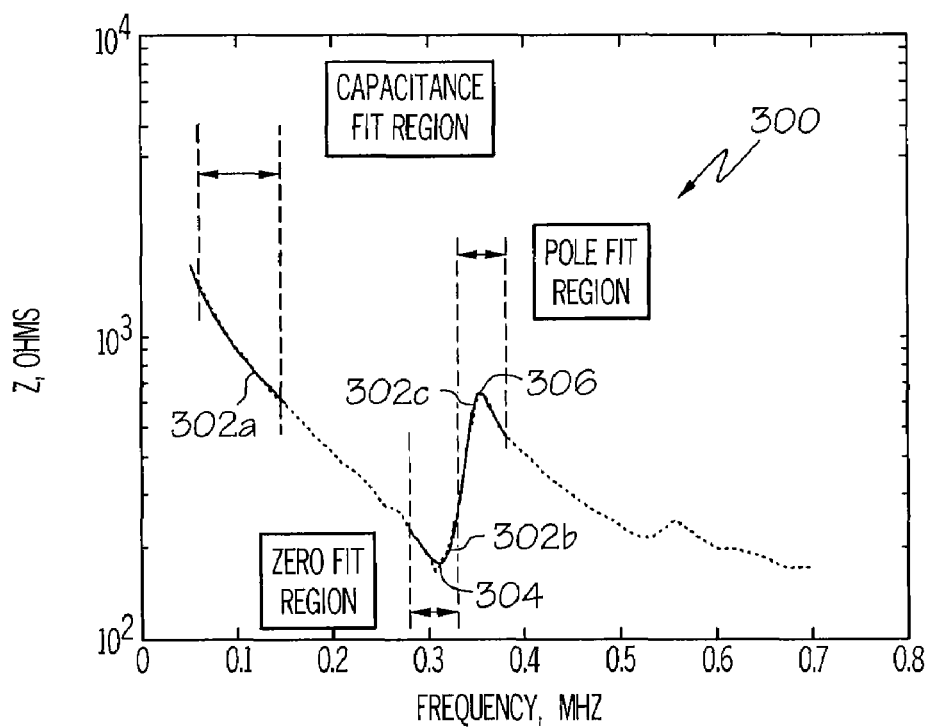
FIG. 3 is an illustration of an example of an impedance curve associated with a transducer and fitting the impedance curve in specific frequency ranges to determine physical parameters for a transducer in accordance with an embodiment of the present invention.

FIG. 3 is an illustration of an example of an impedance curve 300 associated with a transducer and fitting the impedance curve in narrow-band frequency regimes to determine physical parameters for a transducer in accordance with an embodiment of the present invention. The impedance curve 300 is representative of the frequency domain impedance transformed from the current and voltage data received from each transducer and may be characterized or modeled by Equation 1. The bandwidth or frequency range of the curve 300 may correspond to the frequency range or bandwidth of the signal transmitted in block 202. The impedance curve 300 contains information specific to the mechanical properties or parameters of the transducer, such as mechanical properties of the piezoelectric disk of the transducer, the adhesive used to surface-bond the disk to the structure under investigation or being monitored, electrical connection to the transducer as well as other characteristics, properties or parameters.

Referring back to FIG. 2, in block 212, the impedance versus frequency curve (curve 300 in FIG. 3) may be fit in narrow-band regimes or portions to determine physical (electromechanical) transducer (piezo) properties or parameters for each transducer to evaluate the transducer's health. FIG. 3 also illustrates fitting a plurality of curve portions 302 to the impedance curve 300 at selected narrow-band frequency regimes to determine selected physical parameters to diagnose the health of the transducer. The curve fitting may be any type of complex frequency domain (i.e., s-domain) fitting technique that may yield coefficients for the forms or equations in the s-domain. For example, algorithms similar to those described in "Complex-Curve Fitting" by Levi, E. C., IRE Transactions on Automatic Control, Vol. AC-4 (1959), pages 37-44 may be used. However, any generic algorithm to fit data may equally be used.

In block 214 selected parameters may be extracted or determined from the impedance curve 300 using the curve portions 302 fit to the impedance curve 300 at the narrow-band frequency regimes. For example, fitting the curve portion 302a to the shape of the impedance curve 300 at a low frequency portion of the curve 300 (about 50 kHz to about 150 kHz) yields a capacitance of the transducer assuming that Equation 1 is representative or models the impedance curve 300. Capacitance is a function of the transducer electrode area, mechanical boundary condition, and wiring. Fitting the impedance curve at the lower frequency portion may be represented by Equation 2:

$$Z(s) = \frac{1}{sC} \quad \text{Eq. 2}$$

The resonance and anti-resonance peaks of the impedance data or impedance curve 300 may be fit to assume the form of zeros and poles (curve fit portions 302b and 302c, respectively) of the transfer function in Equation 3:

$$Z_{local}(s) = \frac{n_3 s^3 + n_2 s^2 + n_1 s + n_0}{d_3 s^3 + d_2 s^2 + d_1 s + d_0} \quad \text{Eq. 3}$$

The first two roots of the numerator of Equation 3, or zeros of the impedance, can be used to solve for a frequency and a damping term, or sharpness of an anti-resonance peak 304 as provided by Equation 4:

$$s_{zero} = -\zeta_E \omega^E \pm i\omega^E \sqrt{1-\zeta_E^2} \quad \text{Eq. 4}$$

In Equation 4, the frequency in radians at the anti-resonance peak 304 or zero is represented by $\omega^E$ and the damping term is represented by $\zeta_E$.

The first two roots of the denominator of Equation 3, or poles of the impedance, can be used to solve for a frequency and a damping term, or sharpness of a resonance peak 306 as provided by Equation 5:

$$s_{pole} = -\zeta_D \omega^D \pm i\omega^D \sqrt{1-\zeta_D^2} \quad \text{Eq. 5}$$

In Equation 5, the frequency in radians at the resonance peak 306 or pole is represented by $\omega^D$ and the damping term is represented by $\zeta_D$.

A device coupling coefficient $k_{dev}$, defined as the effectiveness of the conversion of mechanical to electrical energy or vice versa, can be determined as a function of the frequency at which the pole and zero occurs as represented by Equation 6:

$$k_{dev}^2 = \frac{(\omega^D)^2 - (\omega^E)^2}{(\omega^D)^2} \quad \text{Eq. 6}$$

Figure 4:
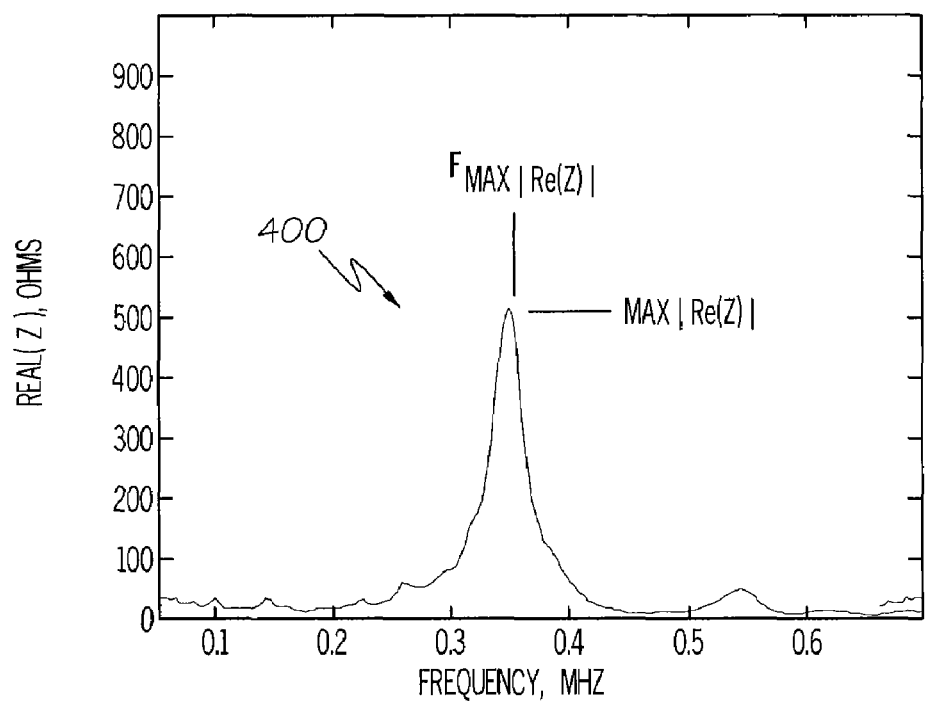
FIG. 4 is an illustration of an example of a curve of the real part of the impedance versus frequency associated with the transducer to determine a maximum of the real part of the impedance and the frequency of the maximum real part of the impedance to determine the health of the transducer in accordance with an embodiment of the present invention.

Other parameters may also be extracted from the impedance data. For example, FIG. 4 is an illustration of an example of a curve 400 of the real part of the impedance versus frequency associated with the transducer to determine a maximum of the real part of the impedance $|(Z(\omega^{max}))|$ and the frequency of the maximum real part of the impedance real $\omega^{max}$ to determine the health of the transducer in accordance with an embodiment of the present invention.

It should be noted that there are many possible failure modes. By extracting a number of parameters and then feeding that combination of parameters into a trained classifier, for example a probabilistic neural network algorithm, the physical condition of the transducer can then be assessed with greater confidence that all possible damage modes are identified.

In block 216, any temperature or other environmental compensation may also be applied to the analysis or in determining the different parameters related to diagnosing the health of each transducer. By plotting the distribution of raw parameters, the diagnostics method is capable of adapting to changes in environmental conditions (e.g. temperature) from previous measurements. It is the deviation from the mean that determines outliers. Thus if the mean shifts due to environmental changes, then the predetermined limits are shifted respectively.

Also in block 216, statistical analysis may be performed to determine the accuracy and reliability of any test data from a particular transducer or group of transducers or sensors in determining the location and size of any anomalies or damage to a structure under investigation or being monitored. Each parameter and/or the percent change in the parameter may be compared to a respective first set of predetermined limits or bounds for each transducer.

In block 218, a determination may be made by a trained classifier as to the state of the transducer. The state of the transducer may fall within three possible classifications: good transducer, partially damaged transducer or bad transducer. Classification could occur by one or more of the following methods: setting predetermined limits, a Bayesian neural network, any rule-based algorithm or other classification method. The classifier determines three states and then three final outcomes respectively. If the transducer is determined as unhealthy, i.e. unusable for damage assessment, that transducer is replaced as shown in block 220. If the transducer is determined as healthy, i.e. no damage, that transducer may be used in the current damage or anomaly assessment of the structure as shown in block 222. If the transducer is determined as marginally damaged or partially damaged, then that transducer is disregarded in the current damage assessment of the structure as shown in block 224, and the diagnostics data from the transducer may be stored for future diagnostics on that transducer and possible future use for damage assessment as shown in block 226.

The flowcharts and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems which perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," and "includes" and/or "including" when used in this specification, specify the presence of stated features, integers, steps, operations, elements, and/or components, but do not preclude the presence or addition of one or more other features, integers, steps, operations, elements, components, and/or groups thereof.

Although specific embodiments have been illustrated and described herein, those of ordinary skill in the art appreciate that any arrangement which is calculated to achieve the same purpose may be substituted for the specific embodiments shown and that the invention has other applications in other environments. This application is intended to cover any adaptations or variations of the present invention. The following claims are in no way intended to limit the scope of the invention to the specific embodiments described herein.

What is claimed is:

1. A method for diagnosing the health of a transducer, comprising:
   transmitting a signal to a transducer to cause the transducer to transmit a stress wave into an object being monitored, wherein the signal has a predetermined frequency range;
   receiving response data for the transducer;
   transforming the response data to data representative of an impedance curve of impedance versus frequency for the predetermined frequency range;
   extracting selected parameters from the impedance curve to diagnose a health of the transducer; and
   fitting a plurality of curve portions to the impedance curve at selected narrow-band frequency regimes to determine selected parameters to diagnose the health of the transducer.

2. The method of claim 1, further comprising:
   measuring a time domain voltage across the transducer and a time domain current through the transducer; and
   transforming the time domain voltage and current into a frequency domain impedance over the predetermined frequency range for the transducer to generate the data representative of the impedance curve.

3. The method of claim 1, wherein extracting selected parameters from the impedance curve comprises determining a capacitance of the transducer.

4. The method of claim 1, further comprising determining a coupling coefficient for the transducer as a function of a frequency at which a pole and a zero of the impedance curve occur.

5. The method of claim 1, wherein extracting selected parameters comprises:

determining a maximum real part of the impedance; and
determining a frequency of the maximum real part of the impedance.

6. The method of claim 1, further comprising fitting one curve portion to a lowest frequency portion of the impedance curve to determine a capacitance of the transducer.

7. The method of claim 1, further comprising:
fitting one curve portion to a resonance peak of the impedance curve to determine a frequency and a damping term of the resonance peak;
fitting another curve portion to an anti-resonance peak of the impedance curve to determine a frequency and a damping term of the anti-resonance peak; and
determining a coupling coefficient for the transducer as a function of the frequency at which the pole and zero of the impedance curve occur.

8. The method of claim 1, further comprising:
fitting a resonance peak portion and an anti-resonance peak portion of the impedance curve to respectively form poles and zeros of a transfer function corresponding to the impedance curve;
determining a frequency and a damping term of the anti-resonance peak from the zeros of the impedance curve;
determining a frequency and a damping term of the resonance peak from the poles of the impedance curve; and
determining a coupling coefficient for the transducer as a function of the frequency at which the pole and zero of the impedance curve occur.

9. The method of claim 1, further comprising:
comparing at least one of each selected parameter and a percent change in the parameter to a set of predetermined limits; and
using any data from the transducer in a current structural health monitoring assessment of the object in response to each selected parameter being within the set of predetermined limits.

10. The method of claim 9, further comprising:
disregarding any data from the transducer in the current structural health monitoring assessment if any one of the at least one of parameters and the percent change in parameters of that transducer does not fall within of its respective predetermined limits;
comparing each selected parameter to a second set of predetermined limits in response to each selected parameter not being within the first set of predetermined limits;
replacing the transducer in response to any one of the parameters of that transducer not falling within a second set of predetermined limits; and
keeping the transducer for future re-assessment and future use in response to all parameters being within the second set of predetermined limits.

11. The method of claim 1, wherein transmitting the signal to the transducer comprises transmitting the signal to each of a plurality of transducers associated with a system for monitoring the structural health of the object.

12. The method of claim 11, further comprising:
determining if each transducer is functioning; and
replacing any non-functioning transducers.

13. The method of claim 12, further comprising conditioning and assessing a signal-to-noise ratio of each transducer.

14. The method of claim 13, further comprising comparing the signal-to-noise ratio (SNR) from a baseline measurement to a second measurement to determine if a change of SNR at a predefined level has occurred.

15. The method of claim 1, wherein transmitting the signal comprises transmitting a long duration broadband signal.

16. The method of claim 1, further comprising determining a state of the transducer.

17. The method of claim 16, wherein determining the state of the transducer comprises classifying the transducer as one of healthy and useable for a current structural health assessment; unhealthy and not useable for the current structural health assessment; and marginal or partially damaged and to disregard data from the transducer in the current structural health assessment and to store the data from the transducer for future diagnostics of the transducer and for possible future use for structural health assessment.

18. The method of claim 17, wherein classifying the transducer comprises one of setting predetermined limits; using a Bayesian neural network; and using a rule-based process.

19. The method of claim 1, further comprising performing temperature or other environmental compensation in diagnosing the health of the transducer or structural health monitoring of the object.

20. A method for monitoring the structural health of an object or structure, comprising:
transmitting a signal to each of a plurality of transducers to cause each transducer to transmit a stress wave into the object or structure being monitored, wherein the signal has a predetermined frequency range;
measuring a time domain voltage across each transducer and a time domain current through each transducer;
transforming the time domain voltage and current into frequency domain impedance over the predetermined frequency range for each transducer to generate data representative of an impedance curve of impedance versus frequency over the predetermined frequency range for each transducer; and
extracting selected parameters from the impedance curve of each transducer to diagnose a health of each transducer; and
fitting a plurality of curve portions to the impedance curve of each transducer at selected narrow-band frequency regimes to determine selected parameters to diagnose the health of each transducer.

21. The method of claim 20, further comprising fitting one curve portion to a low frequency portion of the impedance curve for each transducer to determine a capacitance of each transducer.

22. The method of claim 20, further comprising:
fitting a resonance peak portion and an anti-resonance peak portion of the impedance curve of each transducer to respectively form poles and zeros of a transfer function corresponding to the impedance curve of each transducer;
determining a frequency and a damping term of the anti-resonance peak from the zeros of the impedance curve;
determining a frequency and a damping term of the resonance peak from the poles of the impedance curve; and
determining a coupling coefficient for each transducer as a function of the frequency at which the pole and zero of the impedance curve occur.

23. The method of claim 20, further comprising:
comparing each selected parameter to a set of predetermined limits; and
using any data from each transducer in a current structural health monitoring assessment of the object in response to each selected parameter being within the set of predetermined limits.

24. The method of claim 23, further comprising:
disregarding any data from any of the transducers in a current structural health monitoring assessment object in response to each selected parameter of any of the transducers not being within the set of predetermined limits;

comparing each selected parameter to a second set of predetermined limits in response to each selected parameter not being within the set of predetermined limits;

replacing any transducer in response to each selected parameter not being within the second set of predetermined limits; and storing data from any transducer in response to each selected parameter being within the second set of predetermined limits.

25. The method of claim 20, further comprising determining a state of each transducer.

26. The method of claim 25 wherein determining the state of the transducer comprises classifying the transducer as one of healthy and useable for a current structural health assessment; unhealthy and not useable for the current structural health assessment; and marginal or partially damaged and to disregard data from the transducer in the current structural health assessment and to store the data from the transducer for future diagnostics of the transducer and for possible future use for structural health assessment.

27. The method of claim 20, further comprising compensating for temperature or other environmental conditions in diagnosing the health of the transducer or structural health monitoring of the object.

28. A system for monitoring the structural health of an object or structure, comprising:
a plurality of transducers mounted to the object or structure at chosen locations;
a data acquisition unit electrically connected to each of the transducers;
a module to diagnose a health of each transducer;
a transmitter to transmit a signal to each of the plurality of transducers to cause each transducer to transmit a stress wave into the object or structure being monitored, wherein the signal has a predetermined frequency range;
a meter to measure a time domain voltage across each transducer and a time domain current through each transducer;
a unit to transform the time domain voltage and current into frequency domain impedance over the predetermined frequency range for each transducer to generate data representative of an impedance curve of impedance versus frequency over the predetermined frequency range for each transducer; and
a unit to fit a plurality of curve portions to an impedance curve of each transducer at selected narrow-band frequency regimes to determine selected parameters to diagnose the health of each transducer.

29. The system of claim 28, further comprising:
a unit to extract selected parameters from the impedance curve of each transducer to diagnose a health of each transducer.

30. The system of claim 28, further comprising a shunted resistive network for use in measuring the time domain voltage across each transducer and the time domain current through each transducer.

31. The system of claim 28, further comprising a user interface to control operation of the data acquisition unit, to provide information relative to the health of each transducer, and to provide information relative to the structural health of the object or structure being monitored.

32. The system of claim 28, further comprising a data storage device to store SHM data from any transducer in response to selected parameters for diagnosing the health of any transducer being outside of a first set of predetermined limits and within a second set of predetermined limits.

33. The system of claim 28, further comprising a classifier to classify a state of each transducer as one of healthy and useable for a current structural health assessment; unhealthy and not useable for the current structural health assessment; and marginal or partially damaged and to disregard data from the transducer in the current structural health assessment and to store the data from the transducer for future diagnostics of the transducer and for possible future use for structural health assessment.

34. The system of claim 33, wherein the classifier comprises one of a set of limits predetermined limits; a Bayesian neural network; and a rule-based algorithm.

35. A computer product for diagnosing the health of a transducer comprising a tangible computer readable medium having program code embodied thereon which, when executed by a computer performs a method comprising:
transmitting a signal to each of a plurality of transducers to cause each transducer to transmit a stress wave into the object or structure being monitored, wherein the signal has a predetermined frequency range;
tagging each group of collected data with a metadata tag that includes at least one of a location of the data associated with the metadata tag on the system, a description of the data associated with the metadata tag, and a summary of the data associated with the metadata tag;
measuring a time domain voltage across each transducer and a time domain current through each transducer;
transforming the time domain voltage and current into frequency domain impedance over the predetermined frequency range for each transducer to generate data representative of an impedance curve of impedance versus frequency over the predetermined frequency range for each transducer;
extracting selected parameters from the impedance curve of each transducer to diagnose a health of each transducer; and
fitting a plurality of curve portions to the impedance curve of each transducer at selected narrow-band frequency regimes to determine selected physical parameters to diagnose the health of each transducer.

36. The computer product of claim 35, wherein the computer executed method further comprises fitting one curve portion to a lowest frequency portion of the impedance curve for each transducer to determine a capacitance of each transducer.

37. The computer product of claim 35, wherein the computer executed method further comprises:
fitting a resonance peak portion and an anti-resonance peak portion of the impedance curve of each transducer to respectively form poles and zeros of a transfer function corresponding to the impedance curve of each transducer;
determining a frequency and a damping term of the anti-resonance peak from the zeros of the impedance curve;
determining a frequency and a damping term of the resonance peak from the poles of the impedance curve; and
determining a coupling coefficient for each transducer as a function of the frequency at which the pole and zero of the impedance curve occur.

* * * * *